United States Patent
Dewald et al.

(10) Patent No.: US 12,369,863 B2
(45) Date of Patent: Jul. 29, 2025

(54) NEURAL SIGNAL COMPRESSION FOR BRAIN-MACHINE INTERFACE

(71) Applicant: Neuralink Corp., Fremont, CA (US)

(72) Inventors: Kevin Dewald, Berkeley, CA (US);
Sonal Pinto, Santa Clara, CA (US);
Avinash Jois, Palo Alto, CA (US);
Aram Moghaddassi, Oakland, CA (US)

(73) Assignee: Neuralink Corp., Fremont, CA (US)

( * ) Notice: Subject to any disclaimer, the term of this patent is extended or adjusted under 35 U.S.C. 154(b) by 813 days.

(21) Appl. No.: 17/690,962

(22) Filed: Mar. 9, 2022

(65) Prior Publication Data
US 2023/0284982 A1     Sep. 14, 2023

(51) Int. Cl.
*A61B 5/00*     (2006.01)
*A61B 5/293*    (2021.01)
*A61N 1/05*     (2006.01)
*G06F 3/01*     (2006.01)

(52) U.S. Cl.
CPC .............. *A61B 5/725* (2013.01); *A61B 5/293* (2021.01); *A61B 5/6868* (2013.01); *A61B 5/7282* (2013.01); *A61N 1/0529* (2013.01); *G06F 3/015* (2013.01)

(58) Field of Classification Search
CPC ....... A61B 5/725; A61B 5/6868; A61B 5/293; A61B 5/7282; A61N 1/0529; G06F 3/015
USPC ....................................................... 375/240
See application file for complete search history.

(56) References Cited

U.S. PATENT DOCUMENTS

| | | | |
|---|---|---|---|
| 2003/0043895 A1* | 3/2003 | Melsa | H04L 27/2624 375/340 |
| 2005/0090756 A1* | 4/2005 | Wolf | A61B 5/30 607/48 |
| 2019/0149166 A1* | 5/2019 | Mohajer | H03M 13/2903 341/118 |
| 2021/0012909 A1 | 1/2021 | Koh et al. | |

OTHER PUBLICATIONS

"Goertzel Algorithm," Available Online at: https://en.wikipedia.org/wiki/Goertzel_algorithm, Accessed from Internet on Feb. 24, 2022, 4 pages.
"Haar Transform," Available Online at: https://en.wikipedia.org/wiki/Haar_wavelet#Haar_transform, Accessed from Internet on Feb. 24, 2022, 10 pages.
(Continued)

*Primary Examiner* — Leila Malek
(74) *Attorney, Agent, or Firm* — Oblon, McClelland, Maier & Neustadt, L.L.P.

(57) ABSTRACT

Techniques for compressing neural signals are disclosed herein. The neural signal compression techniques can include lossless compression, lossy compression, binned spike compression, and spike-band power compression. Lossless compression can compress neural signals using a difference predictor to encode compressed neural signals via binary and unary coding. Lossy compression can compress neural signals using quantized wavelet transforms to generate an encoded bit-stream of compressed neural signals. Binned spike and spike-band power compression can leverage the sparse nature of neural signals to threshold the neural signals for generating an appended bit-stream of compressed neural signals.

20 Claims, 8 Drawing Sheets

(56) References Cited

OTHER PUBLICATIONS

"Truncated Binary Encoding," DBpedia, Available Online at: https://dbpedia.org/page/Truncated_binary encoding, Accessed from Internet on Feb. 24, 2022, 3 pages.
"Unary Coding," Academic dictionary, Available Online at: https://en-academic.com/dic.nsf/enwiki/148876), Accessed from Internet on Feb. 24, 2022, 3 pages.
"Wavelet Biorthogonal 2.2 (bior2.2)," Wavelet Browser by Pywavelets, Available Online at: http://wavelets.pybytes.com/wavelet/bior2.2/, Accessed from Internet on Feb. 24, 2022, 6 pages.
Duda, "Asymmetric Numeral Systems: Entropy Coding Combining Speed of Huffman Coding With Compression Rate of Arithmetic Coding," Available Online at: https://arxiv.org/pdf/1311.2540.pdf, Jan. 6, 2014, 24 pages.
Golomb, "Run-Length Encodings," IEEE Transactions on Information Theory, vol. 12, No. 3, Jul. 1966, pp. 399-401.
Huffman, "A Method for the Construction of Minimum-Redundancy Codes," Resonance, Feb. 2006, pp. 91-99.
Jacobsen et al., "The Sliding Dft," IEEE Signal Processing Magazine, vol. 20, No. 2, Mar. 10, 2003, pp. 74-80.
Jacobsen, "Understanding and Implementing the Sliding DFT," Available Online at: https://www.dsprelated.com/showarticle/776.php, Apr. 23, 2015, 7 pages.
Srinivasan, "Lempel-Ziv-Welch," National Institute of Standards and Technology, Available Online at: https://xlinux.nist.gov/dads/HTML/lempelZivWelch.html, Jan. 6, 2022, 1 page.
Starosolski et al., "Modified Golomb-Rice Codes for Lossless Compression of Medical Images," Available Online at: http://sun.aei.polsl.pl/~rstaros/papers/ss2003-eh.pdf, 2003, 16 pages.
Talebi, "The Wavelet Transform: An Introduction and Example," Available Online at: https://towardsdatascience.com/the-wavelet-transform-e9cfa85d7b34, Dec. 21, 2020, 10 pages.
Tatwawadi, "What is Asymmetric Numeral Systems? Understanding the New Entropy Coder Family," Available Online at: https://kedartatwawadi.github.io/post--ANS/, Accessed from Internet on Feb. 24, 2022, 16 pages.

\* cited by examiner

NEURAL SIGNAL COMPRESSION FOR BRAIN-MACHINE INTERFACE

FIELD

This application relates to the field of computing devices, signal compression techniques, and data traffic flow for a brain-machine interface.

BACKGROUND OF THE INVENTION

There are many applications for retrieving signals characterizing activity in the human brain, such as understanding the workings of the brain and sending signals to control prosthetic limbs. For example, key information in a neural signal can be identified based on neural spikes, which are associated with an action potential in a neuron. An action potential, or spike, occurs when a membrane electrical potential rapidly changes. Depolarization and repolarization in the membrane creates a characteristic rise in the voltage across a cell's plasma membrane.

Methods exist for gathering and transmitting data wirelessly. Some methods involve gathering and transmitting data as-a-whole. This can lead to an excessive amount of information and may increase a latency or delay of signal transmission relating to neural signals. Other methods may involve data compression, but the other methods may not be applicable or otherwise feasible for compressing or otherwise handling neural signals.

BRIEF SUMMARY OF THE INVENTION

Some embodiments of the present invention are related to techniques for compressing neural signals via lossless-style techniques. Neural signals can be received via electrodes. The neural signals can be sampled to generate a set of samples. A difference can be computed between each sample and a previous sample. A subset of the samples can be selected based on the difference between each sample and the previous sample. Each sample of the subset of the set of samples can be encoded to generate a unary encoded value and a binary encoded value. The unary encoded values and the binary encoded values can be transmitted for further processing.

The encoding can include, for each sample, computing a factor that minimizes a total size of the encoded sample.

Each unary encoded value can be a quotient computed based on the computed factor. Each binary encoded value can be a remainder corresponding to the quotient. The binary encoded value may be truncated before transmitting.

The techniques described herein may be executed on an integrated circuit that can be communicatively coupled to the electrodes that can be implanted in a brain.

Transmitting the unary encoded values and the binary encoded values can include transmitting the values off of the integrated circuit via a short-range wireless communication system.

Sampling the neural signals can include collecting a frame of 10 or more samples at a sampling rate of between 100 to 1,000 samples per window of 10 milliseconds to 40 milliseconds.

Some embodiments of the present invention are related to a method for compressing neural signals via lossy-style techniques. Neural signals can be received from electrodes. The neural signals can be sampled to generate a set of samples. A wavelet transform can be computed based on the set of samples to generate a wavelet representation of each sample. Each wavelet transform can be quantized to generate a bit-stream. The bit-stream can be encoded to generate a compressed encoded representation of the neural signals.

The neural signals can be filtered and can be fitted to a model to compute a set of values. The set of values can be compared to a respective set of threshold values. A subset of the neural signals that correspond to a neural spike can be selected based on the comparison. The selected subset of the neural signals is used to compute the wavelet transform.

Computing the wavelet transform can include computing a discrete wavelet transform.

The bit-stream can be encoded using range asymmetric numeral systems (rANS).

The techniques disclosed herein can be executed on an integrated circuit that can be communicatively coupled to the electrodes that can be implanted in a brain. The techniques can additionally include transmitting the compressed encoded representation of the neural signals off of the integrated circuit via a short-range wireless communication.

Sampling the neural signals can include collecting a frame of 10 or more samples at a sampling rate of between 100 to 1,00-samples per window of 10 milliseconds to 40 milliseconds.

Some embodiments are related to a method for compressing neural signals associated with sparse representations. Neural signals can be received via electrodes. The neural signals can be sampled to generate a set of samples. A subset of the set of samples having values above a threshold can be identified. A value associated with the subset of the set of samples can be appended to a bit-stream for each of the identified subset. The bit-stream can be transmitted for further processing.

The method can additionally include, before appending the value to the bit-stream, encoding a value of each sample of the identified subset of the set of samples using unary coding to generate an encoded value. The encoded value can be appended to the bit-stream.

The method can additionally include identifying a subset of the neural signals corresponding to a neural spike. The set of samples can be sampled from the subset of the neural signals.

Identifying the subset of the neural signals can include filtering the neural signals, fitting the neural signals to a model to compute a set of values, comparing the set of values to a respective set of threshold values, and selecting (based on the comparison) the subset of the neural signals.

The method can additionally include computing an estimated average power value per sample. The average power value can be the value appended to the bit-stream.

The method can additionally include accumulating filtered neural signals within a time window. The estimated average power value can be computed for the neural signals accumulated within the time window.

The method can additionally include downsampling the filtered neural signals before the accumulating.

The method can be executed on an integrated circuit that can be communicatively coupled to the electrodes. Transmitting the bit-stream for further processing can include transmitting the bit-stream off of the integrated circuit via a short-range wireless communication.

BRIEF DESCRIPTION OF THE DRAWINGS

Illustrative aspects of the present disclosure are described in detail below with reference to the following drawing figures. It is intended that that embodiments and figures disclosed herein are to be considered illustrative rather than restrictive.

DETAILED DESCRIPTION OF THE INVENTION

Figure 1:
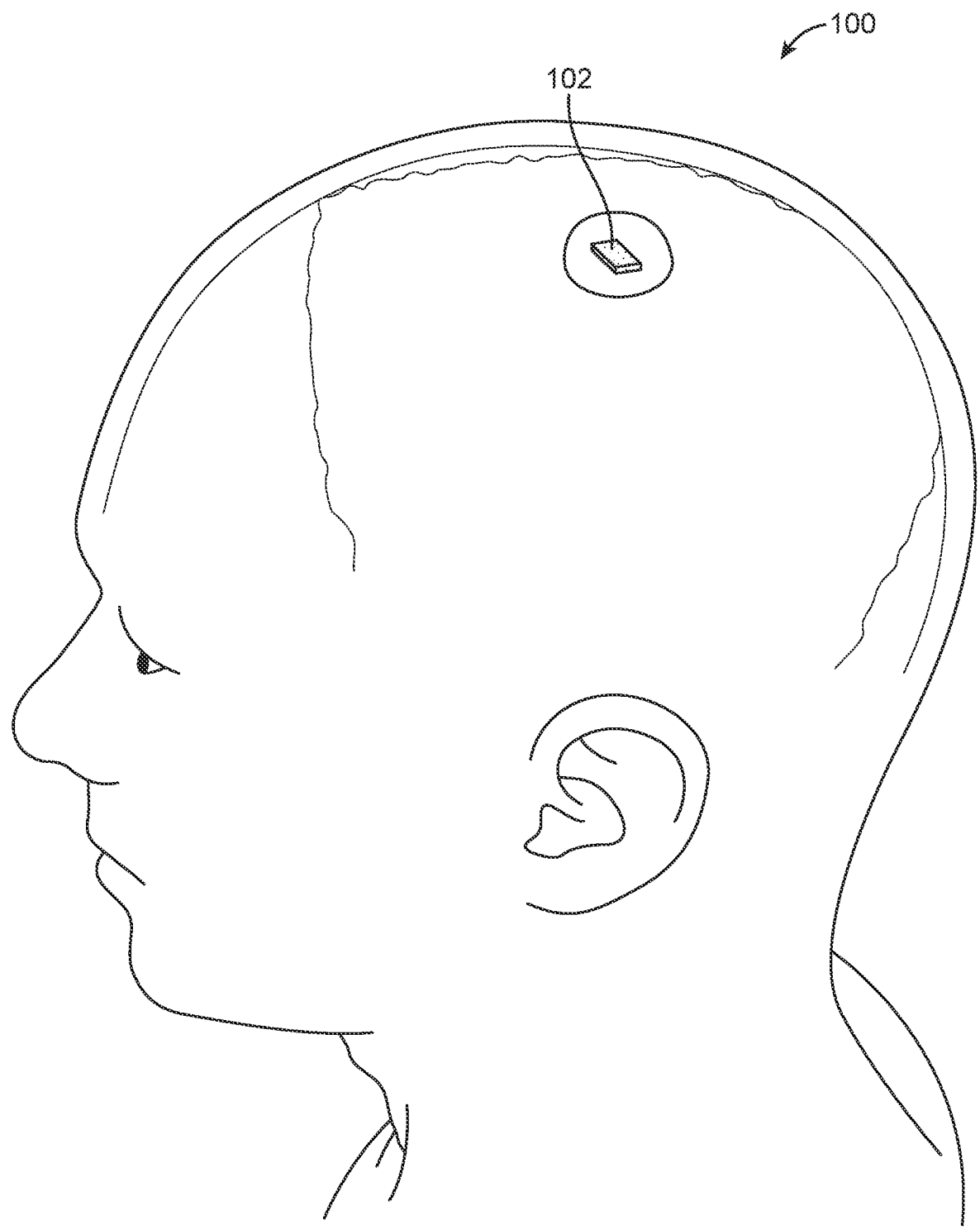
FIG. 1 is a perspective view of an entity having a neural transmitter for gathering and transmitting neural signals in accordance with an embodiment.

Various techniques can be used for compressing neural signals that can be received by a neural transmitter that may be mounted on an entity. The entity can include a human, a non-human primate, a mammal, an invertebrate, or other suitable entity having a brain or other suitable component for generating or transmitting neural signals. The neural transmitter may be mounted abutting or otherwise adjacent to the brain or other similar component of the entity. For example, the neural transmitter can be mounted on a cranium of the entity. The neural transmitter can be used to receive and transmit neural signals. For example, the neural transmitter can receive neural signals from the entity, can compress the neural signals, and can transmit the compressed neural signals for further processing. The neural transmitter can perform the various techniques for neural signal compression. For example, neural signal compression techniques that can be performed by the neural transmitter include lossless compression, lossy compression, binned-spike compression, spike-band power compression, other suitable techniques for neural signal compression, or any suitable combination thereof.

The neural signal compression techniques may correspond to various operational modes of the neural transmitter. For example, the operational modes can include broadband, spike-snippets, binned spikes, spike-band power, and other suitable operational modes of the neural transmitter. The broadband operational mode may involve a set of unfiltered neural signals received by the neural transmitter. The spike-snippets may involve neural signals in close proximity to spikes. The binned spikes and spike-band power operational modes may be used to append values to a bit-stream based on identifying nonzero values in the neural signal data.

The neural transmitter may include a set of operational or communication channels. For example, the neural transmitter can include 128 channels, 256 channels, 512 channels, 1024 channels, 2048 channels, or any other suitable amount of channels. Each channel of the neural transmitter can receive (e.g., from the entity or via an electrode of the neural transmitter) one or more neural signals and can transmit one or more neural signals. In some examples, more than one channel of the neural transmitter can receive and transmit neural signals in parallel. For example, a set of 100 channels of the neural transmitter may receive a set of neural signals and may transmit the received neural signals. Any other suitable amount of channels can be used in parallel by the neural transmitter.

The neural transmitter may receive and transmit the neural signals wirelessly. For example, neural signals (e.g., originating from the brain of the entity or other suitable source) may be received wirelessly via one or more electrodes of the neural transmitter, and the received neural signals may be transmitted wirelessly, for example via Bluetooth® communications or other suitable short-range communication techniques, for further processing. In some examples, the neural signals can be transmitted to a separate or remote computing device for further processing, such as analyzing the neural signals, or for other suitable purposes.

In some examples, receiving and transmitting neural signals can involve an amount or volume of data transfer that may exceed the capability of wireless transmission. For example, if 1000 channels each receive and transmit one or more raw neural signals in parallel, the neural transmitter may encounter an increased amount of latency or processing-time delays due to exceeding the bandwidth of the wireless transmission. In other examples with the amount or volume of data transfer exceeding the capability or bandwidth of wireless transmission, the neural transmitter may not function properly. Additionally, transmitting each raw neural signal of received raw neural signals may be inefficient since a subset of the raw neural signals may be zero or approximately zero (e.g., the subset may not include data relevant or useful enough for using computational resources of the neural transmitter for transmission).

To improve (e.g., reduce) the latency experienced by the neural transmitter, and to improve an efficiency (e.g., reduce a computational cost) of neural signal transmission of the neural transmitter, the neural transmitter may use one or more techniques for compressing neural signals. For example, the neural transmitter may use lossless or lossy compression to compress received raw neural signals (e.g., in a broadband operational mode) or any subset thereof (e.g., in a spike-snippets operational mode). The lossless compression may compress neural signals (e.g., a 3:1 compression using two to four operational channels) for transmitting the neural signals with low latency, high efficiency, and without losing any information. The lossy compression may compress neural signals for transmitting the neural signals with low latency, high efficiency, and by destroying some information that may be considered irrelevant, not useful, or otherwise expendable. Additionally, the neural transmitter may use a binned spikes or spike-power band operational mode to compress received raw neural signals. The neural transmitter may leverage the sparse nature of the received raw neural signals to compress the raw neural signals for reducing latency and increasing efficiency of transmitting neural signals for further processing.

Turning now to the figures, FIG. 1 is a perspective view of an entity 100 having a neural transmitter 102 for gathering and transmitting neural signals in accordance with an embodiment. The entity 100 can include a human, a non-human primate, an invertebrate, a mammal, or any other suitable organism or entity that can receive the neural transmitter 102. For example, the entity 100 can include a brain or similar organ or component that may generate, broadcast, or otherwise include neural signals that can be detected by the neural transmitter 102 or any component thereof.

The neural transmitter 102 can include a set of channels and can operate in various operational modes. For example, the neural transmitter 102 can include 128 channels, 256 channels, 512 channels, 1024 channels, 2048 channels, or any other suitable amount of channels that can each receive and transmit neural signals. Additionally, the operational modes of the neural transmitter 102 can include broadband, spike-snippets, binned spikes, spike-power band, or any other suitable operational mode of the neural transmitter 102. The broadband operational mode may involve the full set of neural signal data, while the spike-snippets operational mode may involve a subset of the neural signal data that includes neural signal data in close proximity to spikes. The binned spikes and spike-power band operational modes may append value to a bit-stream based on identified non-zero values. The binned spikes operational mode may leverage sorting of neural spike values into bins for compression, and the spike-power band operational mode may leverage the average power or amplitude of neural spike values for compression. In some examples, the operational modes of the neural transmitter 102 can correspond to compression techniques used by the neural transmitter 102.

The neural transmitter 102 can receive and transmit neural signals that may originate from the brain or other suitable component of the entity 100. The neural transmitter 102 may receive the neural signals using electrodes, which are shown in and described with respect to FIG. 2, included in or otherwise coupled to the neural transmitter 102. To minimize latency and optimize efficiency, the neural transmitter 102 can compress the received, raw, neural signals using various neural signal compression techniques. For example, the neural transmitter 102 can use lossless compression, lossy compression, and/or sparse compression to compress the raw neural signals prior to transmitting the neural signals. Lossless compression and lossy compression may correspond to the broadband and spike-snippets operational modes for compressing the neural signals with or without, respectively, retaining all of the data of the neural signals. Binned spikes or spike-power band operational modes may be used to append values to a bit-stream based on identifying nonzero values in the neural signal data.

The neural transmitter 102 can receive the neural signals from the entity 100 and can transmit the neural signals for further processing. The neural transmitter 102 can receive the neural signals via one or more electrodes, can compress the neural signals (e.g., using lossless, lossy, or sparse compression), and can transmit the compressed neural signals to a different computing device. For example, the neural transmitter 102 can transmit the compressed neural signals to a computing device, communicatively coupled (e.g., wirelessly coupled) to the neural transmitter 102, that can be used to analyze or otherwise further process the compressed neural signals.

Figure 2:
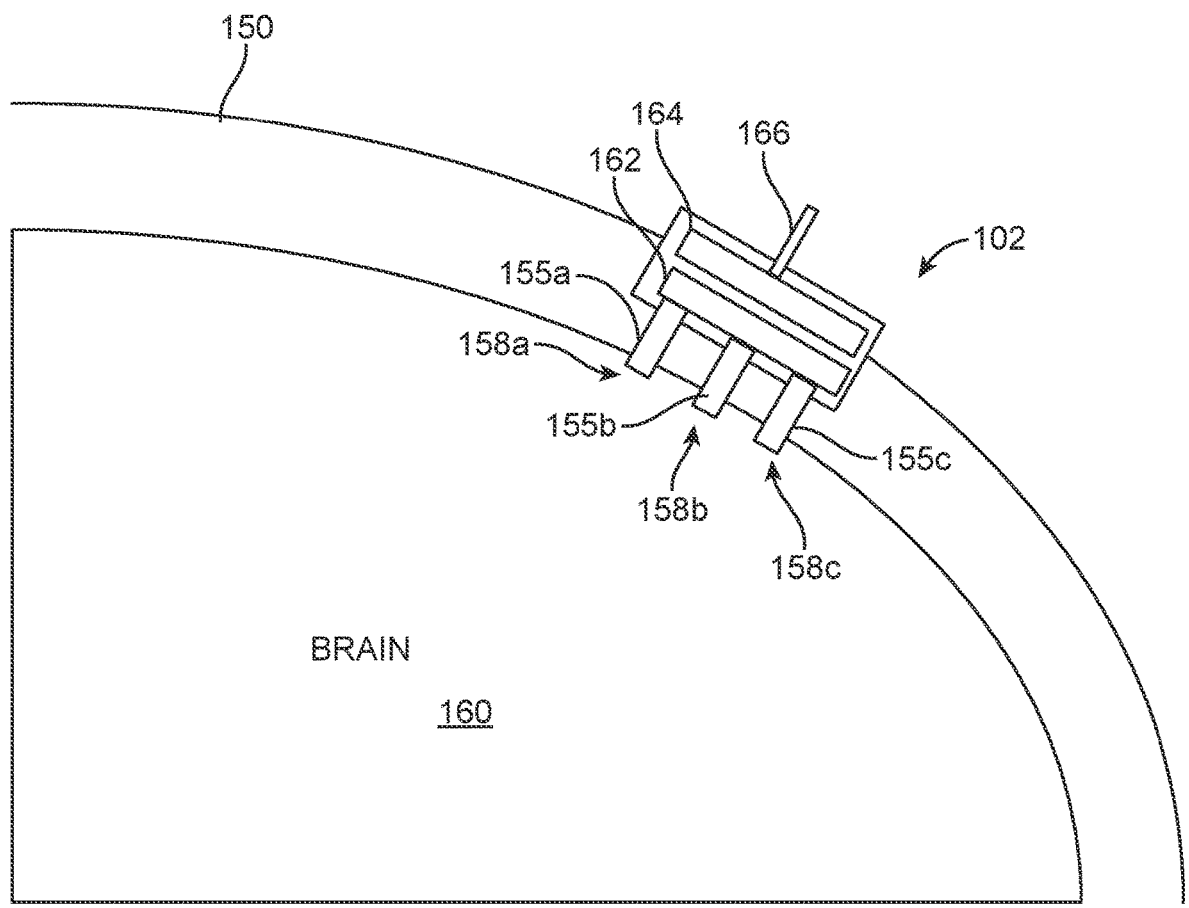
FIG. 2 is a sectional side-view of the neural transmitter of FIG. 1 implanted in a brain of an entity in accordance with an embodiment.

FIG. 2 is a sectional side-view of the neural transmitter 102 of FIG. 1 implanted in a brain 160 of an entity 100 in accordance with an embodiment. As illustrated, the neural transmitter 102 is implanted in the brain 160 of the entity 100 via a cranium 150 of the entity 100. The neural transmitter 102 can be implanted on any other suitable surface of the entity 100 for being implanted in the brain 160 of the entity 100.

The neural transmitter 102 can include a set of electrodes 155a-c, an integrated circuit 162, a short-range communication system 164, and an antenna 166. The neural transmitter 102 can include any other suitable components for receiving, compressing, and transmitting neural signals from the brain 160. Each electrode of the set of electrodes 155a-c can be implanted in a different area of the brain 160. For example, the electrode 155a can be implanted in a first section 158a of the brain 160, the electrode 155b can be implanted in a second section 158b of the brain 160, and the electrode 155c can be implanted in a third section 158c of the brain 160. The set of electrodes 155a-c can be coupled to the integrated circuit 162. For example, the set of electrodes 155a-c can be electrically coupled to the integrated circuit 162, communicatively coupled to the integrated circuit 162, or a combination thereof. The set of electrodes 155a-c can detect or otherwise receive neural signals from the brain and transmit the neural signals to the integrated circuit 162. In some examples, the integrated circuit can compress the neural signals (e.g., using lossless compression, lossy compression, sparse compression, or other suitable compression techniques). The integrated circuit 162 can be suitably coupled to the short-range communication system 164. For example, the integrated circuit 162 can be communicatively coupled to the short-range communication system 164, electrically coupled to the short-range communication system 164, or a combination thereof. The integrated circuit 162 can transmit the compressed neural signals to the short-range communication system 164, which can transmit (e.g., using the antenna 166) the compressed neural signals away from the neural transmitter 102. In some examples, the short-range communication system 164 can transmit the compressed neural signals to a computing system that is separate from the neural transmitter 102 for further processing.

Figure 3:
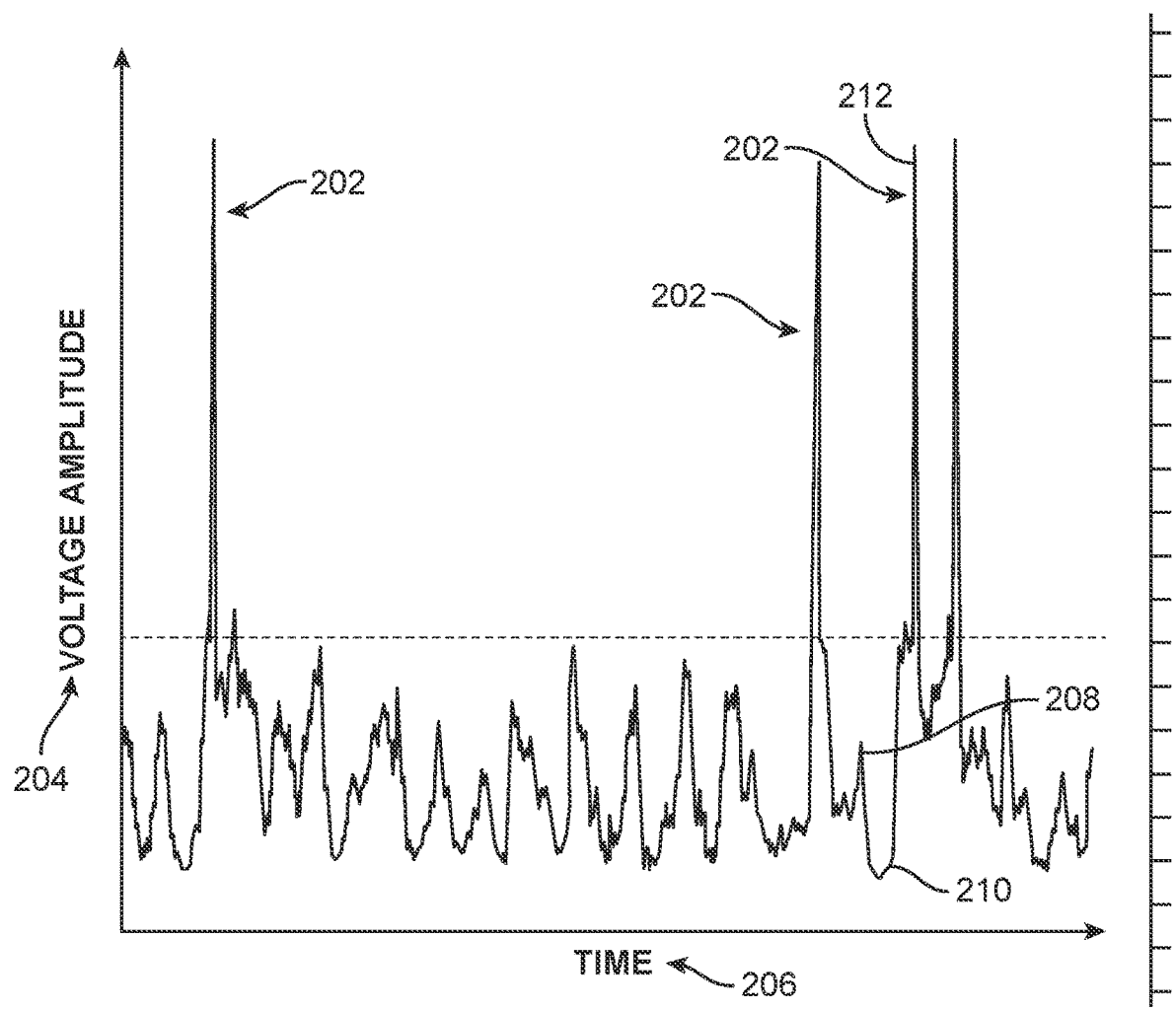
FIG. 3 is an example of biological signals that can be detected and transmitted using the neural transmitter of FIG. 1 in accordance with an embodiment.

FIG. 3 is an example of biological signals that can be detected and transmitted using the neural transmitter 102 of FIG. 1 in accordance with an embodiment. FIG. 3 illustrates an example of a graph 200 of neural voltage over time, including spikes 202 (e.g., neural spikes). Neural spikes are associated with a characteristic change in sample amplitude 204 over time 206. The sample amplitude may, for example, represent voltage, power, or frequency. As a specific example, the sample amplitude 204 is voltage in millivolts (mV).

A spike 202 can be preceded by excitation and inhibition of a membrane. Cells such as neurons can transport electrical signals using action potentials. An action potential is characterized by a voltage change across a cell membrane due to the flow of ions into and out of the neuron. Membranes are permeable to positively and negatively charged ions. The membranes are generally in a resting state. During depolarization, voltage-gated ion channels open due to an electrical stimulus. As ions rushes back into the cell, the charged ions modify the charge inside the cell (e.g., an influx of positive sodium ions raise the charge inside the cell from negative to positive). If a threshold is reached, then an action potential is produced. Once the cell has been depolarized, the voltage gated ion channels close. As charged ions exit the cell, the membrane potential falls and starts to approach the resting potential. Typically, repolarization overshoots the resting membrane potential, making the membrane potential more negative (hyperpolarization). An action potential is followed by a refractory period.

As illustrated in FIG. 3, a spike 202 can be characterized by characteristic rises and falls in sample amplitude. A signal may start out with an initial resting value, followed by a first positive change in sample amplitude 208, followed by a reduction in sample amplitude 210 below the resting value, and a second positive change in sample amplitude 212. The second positive change in sample amplitude 212 is generally greater than the first positive change in sample amplitude 208. In some embodiments, spikes in a biological signal are viewed in a shape space based on these characteristic changes in sample amplitude over time.

In some examples, a spike 202 (e.g., as illustrated in FIG. 3) can be included in, or otherwise associated with, neural signals. The neural signals may originate from the entity 100, or other suitable source of neural signals, and the neural transmitter 102 may detect (e.g., using the set of electrodes 155a-c, etc.) the neural signals including the spike 202. In some examples, the spike 202 may be preceded by, or proceeded by, neural signals that are not spikes such as neural signals that are close to or equal to zero or constant, etc. In some examples, the spike 202 may cause the neural transmitter 102 to choose or otherwise operate in one or more operational modes for compressing the received neural signals. For example, if the neural transmitter 102 receives the neural signals having the spike 202, the neural transmitter 102 may operate in a spike-snippets operational mode in which neural data in close proximity to the spike 202 is preserved and compressed for transmitting compressed neural signals.

Figure 4:
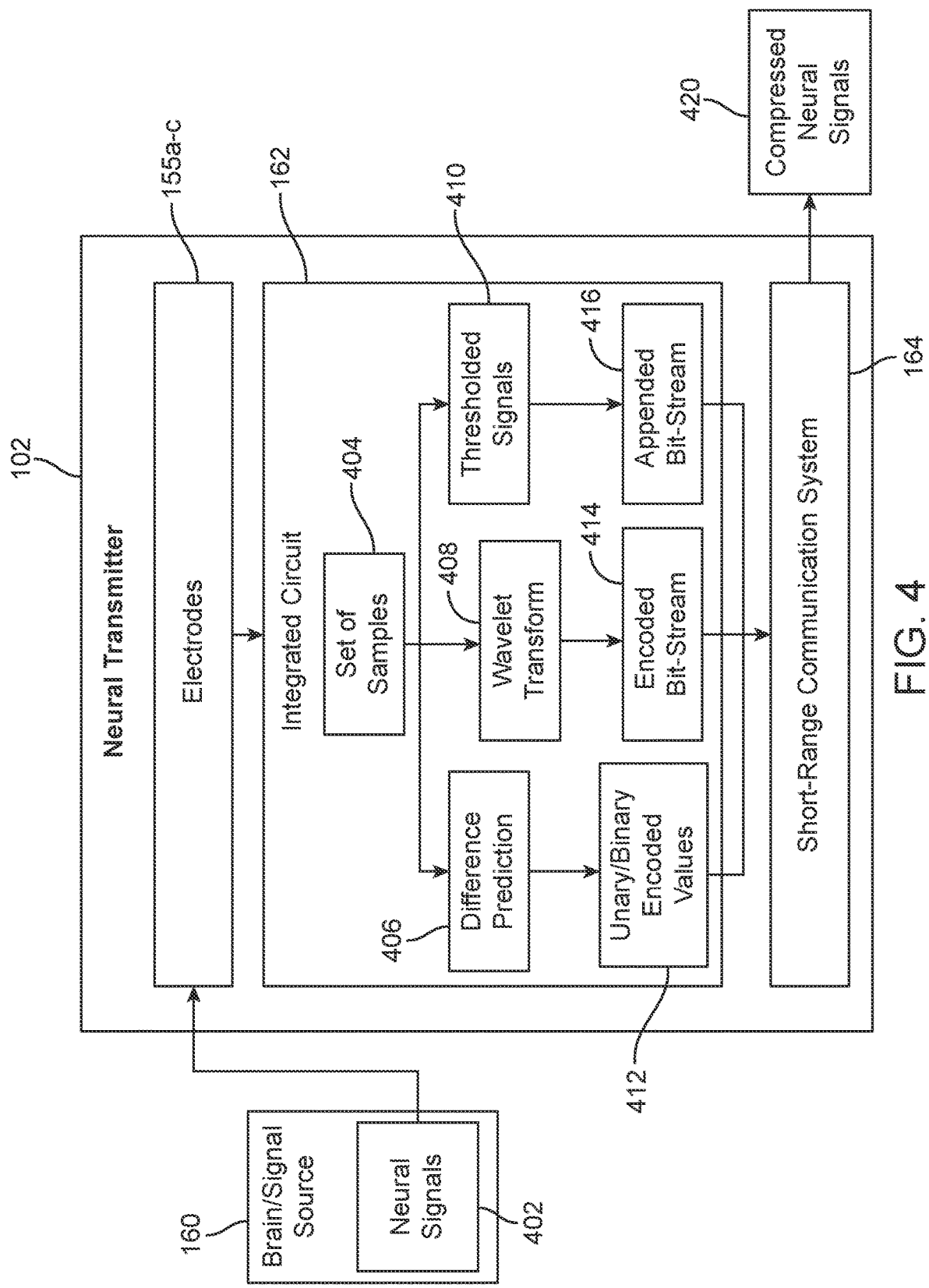
FIG. 4 is a flow diagram of an example flow of neural signals through the neural transmitter of FIG. 1 in accordance with an embodiment.

FIG. 4 is a flow diagram of an example flow of neural signals 402 through the neural transmitter 102 of FIG. 1 in accordance with an embodiment. The neural signals 402 can be generated by the brain 160 or other suitable source of the neural signals 402. The set of electrodes 155a-c can detect or otherwise receive the neural signals 402 from the brain 160. The set of electrodes 155a-c can subsequently transmit the neural signals 402 to the integrated circuit 162.

The integrated circuit 162 can compress the neural signals 402. For example, the integrated circuit 162 can generate a set of samples 404 by sampling the neural signals 402. The set of samples 404 can be generated by the integrated circuit 162, or other suitable device or subset thereof, generating at least 10 samples of the neural signals 402 at a sampling rate of from 100 to 1,000 samples per window. The window may include or otherwise be characterized by a time frame of from 10 milliseconds to 40 milliseconds. The sampling rate, the window, or a combination thereof may include or be characterized by any other suitable ranges or values (e.g., less than 100 samples per window, greater than 1,000 samples per window, less than 10 milliseconds, greater than 40 milliseconds, etc.). In some examples, the integrated circuit 162 can use the set of samples 404 to compress the neural signals 402 via lossless compression, lossy compression, sparse compression, other suitable compression techniques or any combination thereof.

In some modes of operation, such as broadband or spike snippet modes for lossless compression, the integrated circuit 162 can use the set of samples 404 to determine a difference prediction 406 with respect to the neural signals 402 or any samples thereof. The difference prediction 406 can involve the integrated circuit 162 determining a difference between each sample and a previous sample for predicting samples. The predicted samples that are accurate may not be directly transmitted by the neural transmitter 102, while the samples of the set of samples 404 for which the difference prediction 406 is inaccurate may be directly transmitted by the neural transmitter 102. The difference prediction 406 can allow the integrated circuit 162 to generate encoded values 412. The encoded values 412 can include unary encoded values and binary encoded values. For example, the unary encoded values can be a quotient calculated with respect to the difference prediction 406 and the binary encoded values can be a remainder determined with respect to the quotient. The integrated circuit 162 can transmit the encoded values 412 to the short-range communication system 164.

In some modes of operation, such as broadband or spike snippets modes for lossy compression, the integrated circuit 162 can use the set of samples 404 to determine a wavelet transform 408 with respect to the neural signals 402 or any samples thereof. The wavelet transform 408 can be or otherwise include a discrete wavelet transform (e.g., using a biorthogonal 2.2 wavelet or other suitable wavelet for the discrete wavelet transform). Details about the neural signals 402 can be corresponded to frequencies determined in the wavelet transform 408. In some examples, a subset of the set of samples 404 can be selected for determining the wavelet transform 408. The integrated circuit 162 can use the wavelet transform 408 to generate an encoded bit-stream 414. For example, the integrated circuit 162 can quantize each wavelet transform 408 of the set of samples 404, and the integrated circuit 162 can encode the quantized wavelet transforms and append the quantized wavelet transforms to the encoded bit-stream 414. The integrated circuit 162 can transmit the encoded bit-stream 414 to the short-range communication system 164.

In some modes of operation, such as sparse mode, the integrated circuit 162 can use the set of samples 404 to determine a set of values that can be compared against threshold signals 410 with respect to the neural signals 402 or any samples thereof. The integrated circuit 162 can compare the set of values to the threshold signals 410 for determining whether the set of samples 404 corresponds to a neural spike, whether the set of samples 404 is a sparse set of samples, or a combination thereof. Upon comparison, the integrated circuit 162 can filter the set of samples 404 or the neural signals 402 and can encode (e.g., using unary coding or other suitable encoding techniques) the filtered neural signals. The integrated circuit 162 can append the encoded values to generate an appended bit-stream 416. The integrated circuit 162 can transmit the appended bit-stream 416 to the short-range communication system 164.

The integrated circuit 162 can transmit the encoded values 412, the encoded bit-stream 414, the appended bit-stream 416, or any suitable combination thereof to the short-range communication system 164. The short-range communication system 164 can use short-range communication technology (e.g., Bluetooth, and the like) to transmit (e.g., using the antenna 166) the encoded values 412, the encoded bit-stream 414, the appended bit-stream 416, or any suitable combination thereof as compressed neural signals 420. For example, the short-range communication system 164 can transmit the compressed neural signals 420 to a separate computing device for further processing or for other suitable purposes.

FIGS. 5-8 are flowcharts of processes 500-800 for neural signal compression according to some embodiments. In some implementations, each of the processes 500-800 corresponds to a different operating mode for the neural transmitter. The process 500 of FIG. 5 can be used for a lossless form of compression, and the process 600 of FIG. 6 can be used for a lossy form of compression. For both forms of compression, signals can be obtained in raw waveforms from neural sensors. In some implementations, signal processing is applied to the waveforms (e.g., filtering, decimation, downscaling, etc.). The process 700 of FIG. 7 can be used for a binned spike mode of operation, where spike events may be counted within windows of time. The process 800 of FIG. 8 can be used for a spike-band power mode of operation, where waveforms may be accumulated and averaged within a time window. The neural transmitter may transition between the four operating modes as appropriate. One, two, three, or all four operating modes may be used.

Figure 5:
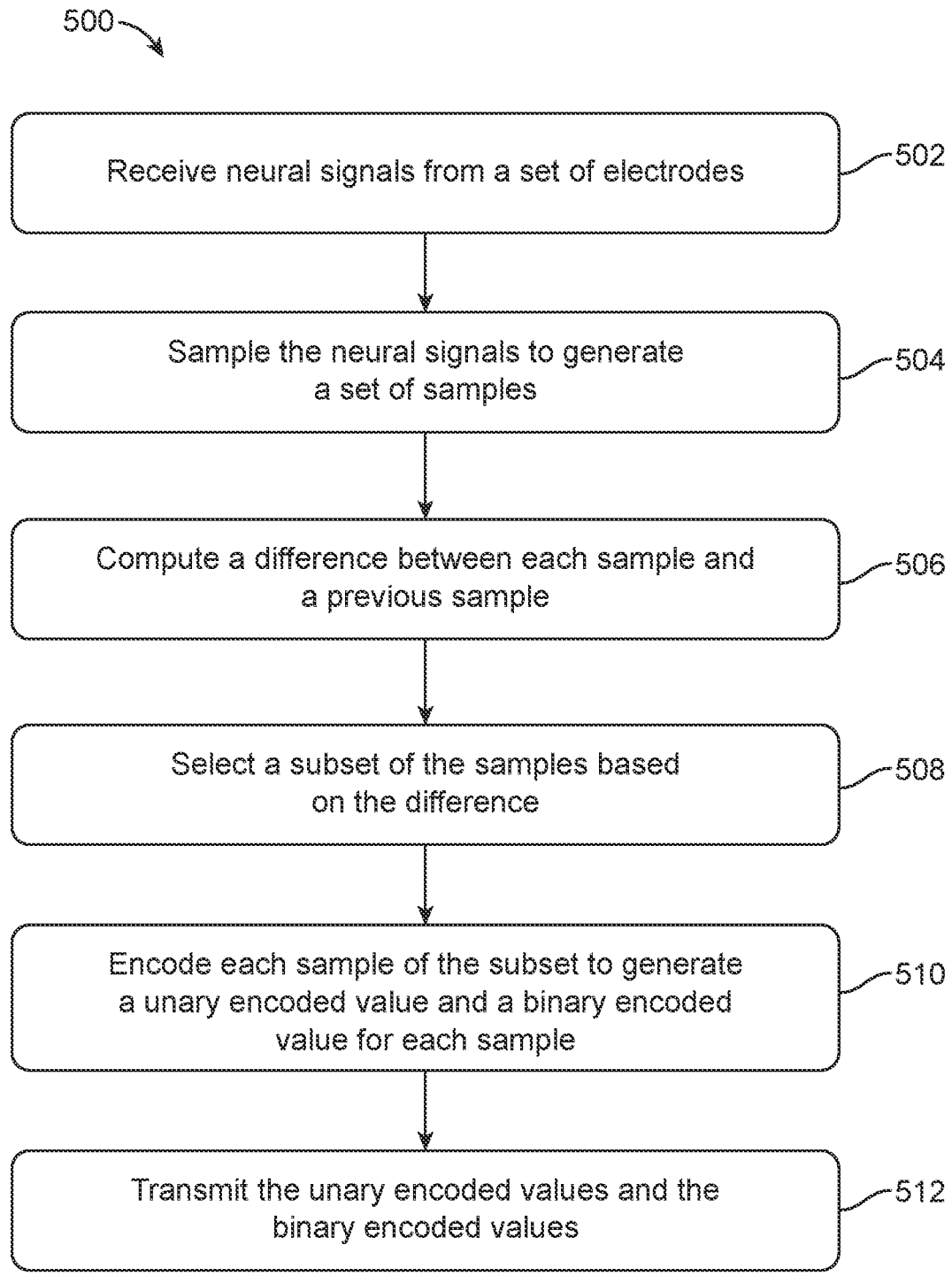
FIG. 5 is a flowchart of a process to compress and transmit neural signals using a lossless operational mode in accordance with an embodiment.

FIG. 5 is a flowchart of a process 500 to compress and transmit neural signals using a lossless operational mode in accordance with an embodiment. In some examples, the process 500 can be used with respect to a broadband operational mode or a spike-snippets operational mode of the neural transmitter 102. In the broadband operational mode, the process 500 is applied to raw waveforms as measured. In the spike-snippets operational mode, the process 500 is applied to portions of the raw waveform around an event of interest (e.g., a neural spike). One or more operations of the process 500 can be performed by the neural transmitter 102, any component thereof, or any other suitable device (e.g., computing device) suitably coupled to the neural transmitter 102. The neural transmitter 102 may be or may otherwise include an integrated circuit 162 that can be communicatively coupled to a set of electrodes 155 that can be implanted in (or otherwise suitably coupled to) a brain 160 (or other suitable component) of the entity 100.

In operation 502, neural signals are received from one or more electrodes. The electrodes can be included in, or otherwise (e.g., communicatively or electrically) coupled, to the neural transmitter 102. In some examples, the electrodes can detect neural signals (e.g., spikes) from the entity 100 (or any component thereof such as a brain of the entity 100). The electrodes may detect or otherwise receive the neural signals and may transmit the neural signals to the neural transmitter 102 for processing (e.g., compressing).

In operation 504, the neural signals are sampled to generate a set of samples. The neural transmitter 102, or other suitable device or subset thereof, can variously sample the neural signals. For example, the neural transmitter 102 can gather or otherwise receive 20,000 samples per second, or 500 samples in 20 milliseconds, to generate the set of samples. In other examples, the neural transmitter 102 may generate a frame or a set of samples of size 16 from the neural signals received in the operation 502. The sampling may involve the neural transmitter 102, or other suitable device or subset thereof, generating at least 10 samples, of the neural signals, at a sampling rate of from 100 to 1,000 samples per window. The window may include or otherwise be characterized by a time frame of from 10 milliseconds to 40 milliseconds. The sampling rate, the window, or a combination thereof may include or be characterized by any other suitable ranges or values (e.g., less than 100 samples per window, greater than 1,000 samples per window, less than 10 milliseconds, greater than 40 milliseconds, etc.).

In some implementations (e.g., for spike snippets mode), the neural transmitter 102 can filter the neural signals. For example, the neural transmitter 102 can filter, remove, or otherwise ignore neural signals that are not in close proximity to, or otherwise associated with, a neural spike. The filtered neural signals can be fitted, by the neural transmitter 102, to a model to compute a set of values such as in U.S. Patent Application Publication Number US 2021/0012909 A1, titled "Real-Time Neural Spike Detection," the entirety of which is hereby incorporated by reference. For example, the neural transmitter 102 can fit the filtered neural signals to a polynomial. In other examples, the neural transmitter 102 may apply a local smoothing functions (e.g., Brown's double exponential smoothing function) to the filtered neural signals. The model may represent or otherwise correspond to a neural spike, and the set of values may include characteristic values that can be determined from the fitted values.

The set of values can be compared to a respective set of threshold values, which can include values above (or below) which the neural signals can be considered associated with or included in a neural spike. The neural transmitter 102 can select a subset of the neural signals that correspond to values that are above the threshold values and that indicate that the neural signals are part of a neural spike. In some implementations, the neural signals associated with the neural spikes are also sorted into different categories (e.g., based on a shape of the spike or other criteria). The subset of the neural signals can be used by the neural transmitter 102 to perform one or more of operations 506-512.

In operation 506, a difference between each sample of the set of samples and a previous sample is determined. For each sample determined in the operation 504, the neural transmitter 102, or other suitable computing device or subset thereof, can determine a difference between the sample and a previous sample. The previous sample can be a sample from or included in a previous set of samples determined (e.g., or transmitted) by the neural transmitter 102. The difference between some samples of the set of samples and a corresponding previous sample may be zero or approximately zero, and the difference between other samples of the set of samples and the corresponding previous sample may be nonzero. In some examples, the neural transmitter 102 computes the difference using a difference predictor given by:

$$y[n]=x[n]-x[n-1] \qquad [1],$$

where x is an input signal and y is an output signal, and n is an index for each signal. If a sample is the same as a previous sample, then the difference value is zero. If a sample is different from a previous sample, then the difference value is nonzero.

In operation 508, a subset of the set of samples is selected based on the difference determined at the operation 506. In some implementations, the difference computed at operations 506 (e.g., the difference predictor of Equation [1]) is used to select values where the difference is nonzero. This can be used to reduce duplicative data by identifying samples with different values than a previous sample. Those values with a zero-valued difference can then be discarded or disregarded, so that there is no need to transmit multiple consecutive samples with the same value. This is particularly useful for neural signals, for which often most signals received are zero or close to zero. Applying the difference predictor to select the subset of the set of samples can, for example, reduce the size of each value from between 6-7 bits of information per symbol to 5-4 bits per symbol.

In operation 510, each sample of the subset of the set of samples is encoded to generate a unary encoded value and a binary encoded value. The neural transmitter 102, or other suitable device or subset thereof, can compute a factor that minimizes a total size of each encoded sample. In some examples, the factor may include a measure of entropy of the samples. In some examples, the encoding can be performed by the neural transmitter 102 using Rice-Golomb coding or other suitable techniques. For example, the neural transmitter 102 can use Rice-Golomb coding to determine, based on the computed factor, a quotient and a remainder. The quotient can be or otherwise include the unary encoded value, and the remainder can correspond to the quotient and can be or otherwise include the binary encoded value. Given a constant M, a symbol S (e.g., the value being encoded) can be represented as a quotient (Q) and remainder (R), where:

$$S=Q \times M+R \qquad [2].$$

The quotient is given by $$Q = \left\lceil \frac{X}{M} \right\rceil \quad [3]$$

and the remainder is given by $$R = X - QM \quad [4].$$

M can be selected using a Bernoulli process to predict an M value to minimize the total size of the encoded sample. Rice-Golomb coding techniques are described further in Golomb, S. W., "Run-Length Encodings," *IEEE Transactions on Information Theory*, IT-12, pp. 399-401 (1966) and Starosolski, R., "Modified Golomb-Rice Codes for Lossless Compression of Medical Images" (2003). The quotient Q is encoded using unary coding (e.g., by writing a Q-length string of 1 bit or 0 bits and writing a 0 bit, as described in Academic dictionary at https://en-academic.com/dic.nsf/enwiki/148876). In some implementations, before applying unary coding, the neural transmitter 102 determines the maximum value that needs to be coded and adjusts the total number of necessary bits accordingly. The remainder R is encoded using truncated binary encoding (e.g., as described in DBpedia at https://dbpedia.org/page/Truncated_binary_encoding). For real-time, on-chip, subject-implanted compression, it is important to both achieve a high compression ratio, as well as keep the complexity of implementation low to keep power usage and space to a minimum. It has been found that Rice-Golomb coding is particularly suitable for this particular application, as Rice-Golomb coding achieves good compression with relatively low computational cost.

In operation 512, the unary encoded values and the binary encoded values are transmitted. The neural transmitter 102 can transmit the unary encoded values and the binary encoded values to one or more separate computing devices for further processing (e.g., analysis, evaluation, etc.). For example, the neural transmitter 102 can transmit the unary encoded values and the binary encoded values off of the integrated circuit (e.g., to the separate computing device) via a short-range wireless communication system. Using Bluetooth® as the transmission medium, the process 500 can be used to transmit between 2 and 4 channels simultaneously, with an approximately 3:1 compression ratio. In some implementations, the encoded values are transmitted to an external computing device for further analysis. The external computing device may then decode the encoded values. Decoding the encoded values may be executed essentially by reversing the encoding process described above with respect to steps 502-512.

Figure 6:
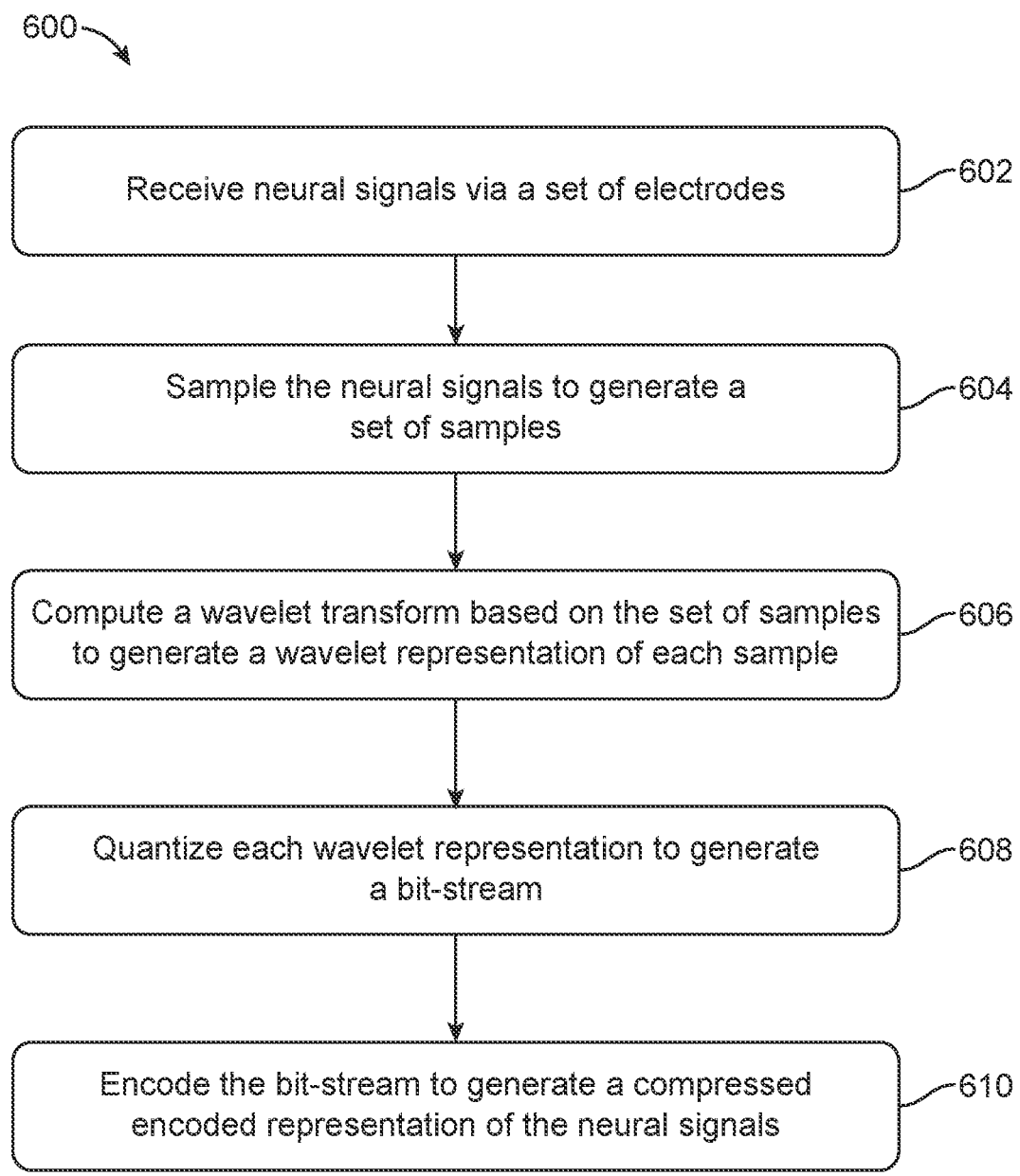
FIG. 6 is a flowchart of a process to compress and transmit neural signals using a lossy operational mode in accordance with an embodiment.

FIG. 6 is a flowchart of a process 600 to compress and transmit neural signals using a lossy operational mode in accordance with an embodiment. In some examples, the process 600 can be used with respect to a broadband operational mode or a spike-snippets operational mode of the neural transmitter 102. In the broadband operational mode, the process 600 is applied to raw waveforms as measured. In the spike snippets operational mode, the process 600 is applied to portions of the raw waveform around an event of interest (e.g., a neural spike). One or more operations of the process 600 can be performed by the neural transmitter 102, any component thereof, or any other suitable device (e.g., computing device) suitably coupled to the neural transmitter 102. The neural transmitter 102 may be or otherwise include an integrated circuit 162 that can be communicatively coupled to a set of electrodes 155 that can be implanted in (or otherwise suitably coupled to) a brain 160 (or other suitable component) of the entity 100.

In operation 602, neural signals are received from one or more electrodes. The electrodes can be included in, or otherwise (e.g., communicatively or electrically) coupled, to the neural transmitter 102. In some examples, the electrodes can detect neural signals (e.g., spikes) from the entity 100 (or any component thereof such as a brain of the entity 100). The electrodes may detect or otherwise receive the neural signals and may transmit the neural signals to the neural transmitter 102 for processing (e.g., compressing).

In some implementations (e.g., for spike snippets mode), the neural transmitter 102 can select a subset of the neural signals corresponding to a neural spike, which may include filtering the neural signals, fitting the filtered neural signals to a model to compute a set of values, and selecting a subset of the neural signals corresponding to a neural spike, as described in further detail above with respect to operation 502 of FIG. 5. The selected subset of the neural signals can be used to perform one or more of operations 604-610, including computing the wavelet transform at operation 606.

In operation 604, the neural signals are sampled to generate a set of samples. The neural transmitter 102, or other suitable device or subset thereof, can variously sample the neural signals. For example, the neural transmitter 102 can gather or otherwise receive 20,000 samples per second, or 500 samples in 20 milliseconds, to generate the set of samples. In other examples, the neural transmitter 102 may generate a frame or a set of samples of size 16 from the neural signals received in the operation 602. The sampling may involve the neural transmitter 102, or other suitable device or subset thereof, generating at least 10 samples, of the neural signals, at a sampling rate of from 100 to 1,000 samples per window. The window may include or otherwise be characterized by a time frame of from 10 milliseconds to 40 milliseconds. The sampling rate, the window, or a combination thereof may include or be characterized by any other suitable ranges or values (e.g., less than 100 samples per window, greater than 1,000 samples per window, less than 10 milliseconds, greater than 40 milliseconds, etc.).

In operation 606, a wavelet transform is determined based on the set of samples for generating a wavelet representation of each sample of the set of samples. The neural transmitter 102 can perform or otherwise determine a wavelet transform (e.g., similar to a Fourier transform) with respect to the set of samples. The wavelet transform can be or otherwise include a discrete wavelet transform (DWT) by decomposing the signal into a number of sets of time series of coefficients describing the time evolution of the signal in the corresponding frequency band, as described in Shawhim Talebi, "The Wavelet Transform," *Towards Data Science*, available at https://towardsdatascience.com/the-wavelet-transform-e9cfa85d7b34 (2020). As a specific example, a biorthogonal 2.2 (bior 2.2) wavelet or other suitable wavelet can be used for the discrete wavelet transform (See "Wavelet Biorthogonal 2.2," *Wavelet Browser*, http://wavelet-s.pybytes.com/wavelet/bior2.2/). Details (e.g., amplitude, etc.) about the neural signals can be corresponded to frequencies determined in the wavelet transform. In some examples, a subset of the set of samples can be selected for determining the wavelet transform.

In operation 608, each wavelet representation (e.g., determined at the operation 606) is quantized for generating a bit-stream. The neural transmitter 102 can quantize each wavelet representation, for example, by restricting each wavelet representation into discrete values (e.g., unary or binary values). In some examples, probability mass function (PMF) quantization can be performed by the neural transmitter 102 for quantizing the wavelet representations. The details about the neural signals that have been corresponded to the frequencies of the wavelet representations can be quantized by the neural transmitter 102. Quantizing the details may reduce an amount of bits or computational resources used for each detail. In some examples, most information about the details of the neural signals may be stored corresponding to lower frequencies of the wavelet representation, while the higher frequencies of the wavelet representation include fewer, or close to zero, information.

In operation 610, the bit-stream is encoded to generate a compressed, encoded representation of the neural signals. In some examples, the details (e.g., each being single numerical values) included in the wavelet representations can be appended to the bit-stream. The bit-stream can be encoded by the neural transmitter 102 using range asymmetric numeral systems (rANS). (See, e.g., Kedar Tatwawadi, "What is Asymmetric Numeral Systems," *Github*, https://kedartatwawadi.github.io/post--ANS/). In some examples, the neural transmitter 102 can use an application of rANS for encoding the bit-stream. The application of rANS may include a fast rANS (frANS) technique in which some constraints (e.g., PMF quantization) can be relaxed. Relaxing some constraints may cause loss in a marginal amount of data (e.g., since this compression technique is "lossy"), but accuracy loss due to the marginal data loss may be negligible. rANS is an entropy coding method, meaning that compression using rANS relies on accurate distribution of spike counts per bin. The main configurable parameters that influence the spike count distribution are spike categories and neural sensor parameters. Application of rANS to binned-spikes data can provide an 8:1 compression ratio without tracking different spike categories or 23:1 compression ratio with tracking the different spike categories.

In some implementations, on-chip (e.g., on the neural transmitter 102) calculation of spike counts is performed to generate a dynamic codebook which is uploaded to the neural transmitter during a session. This method can be applied to any user configuration and underlying spike rate distribution. Alternatively, or additionally, off-chip calculation is performed as described below.

Upon encoding the bit-stream, the neural transmitter 102 may transmit the neural signals (e.g., via the encoded bit-stream). For example, the neural transmitter 102 may transmit the neural signals to a separate computing device (e.g., for further processing such as signal analysis) using a short-range wireless communication system or network. Using Bluetooth® as the transmission medium, the process 600 can be used to transmit between 4 and 8 channels simultaneously, with an approximately 6:1 compression ratio. In some examples, the separate computing device, or other suitable target for transmitting the neural signals via the bit-stream, can decode the bit-stream in an equal-but-opposite process compared to encoding the bit-stream.

In some implementations, the compressed, encoded representation is transmitted to an external computing device for further analysis. The external computing device may then decode the compressed, encoded representation. Decoding the compressed, encoded representation may be executed essentially by reversing the process described above with respect to steps 604-610. In some implementations, analysis of spike data is performed on the external computing device to generate a static codebook which is compiled into firmware. This codebook may apply to a specific user configuration and underlying spike rate distribution.

Figure 7:
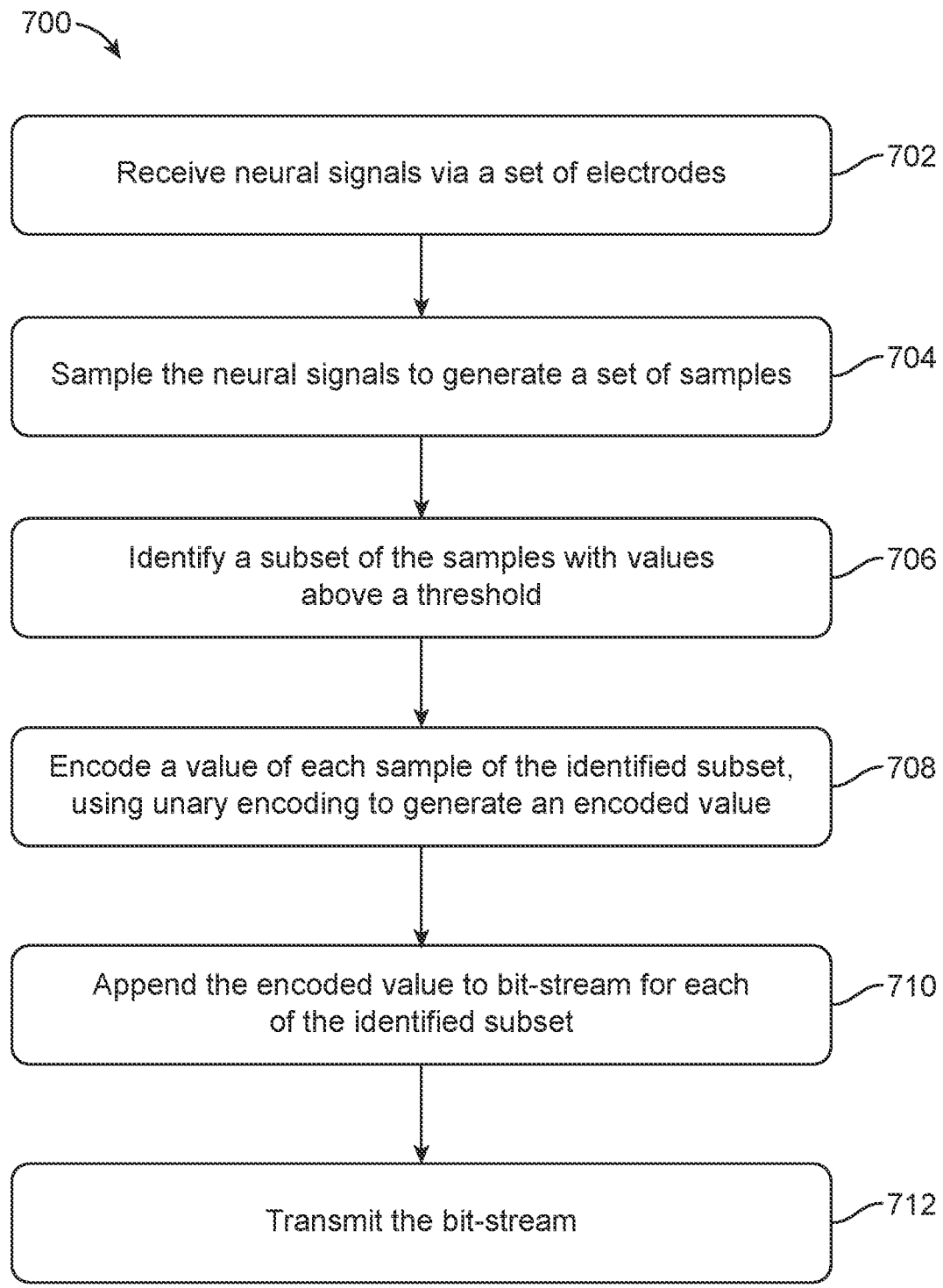
FIG. 7 is a flowchart of one example of a process to compress and transmit sparse neural signals in accordance with an embodiment.

FIG. 7 is a flowchart of one example of a process 700 to compress and transmit sparse neural signals in accordance with an embodiment. In some examples, the process 700 can be used with respect to a binned-spikes operational mode of the neural transmitter 102. One or more operations of the process 700 can be performed by the neural transmitter 102, any component thereof, or any other suitable device (e.g., computing device) suitably coupled to the neural transmitter 102.

In operation 702, neural signals are received from one or more electrodes. The electrodes can be included in, or otherwise (e.g., communicatively or electrically) coupled to, the neural transmitter 102. In some examples, the electrodes can detect neural signals (e.g., spikes) from the entity 100 (or any component thereof such as a brain of the entity 100). The electrodes may detect or otherwise receive the neural signals and may transmit the neural signals to the neural transmitter 102 for processing (e.g., compressing).

In some implementations, the neural transmitter 102 can select a subset of the neural signals corresponding to a neural spike, which may include filtering the neural signals, fitting the filtered neural signals to a model to compute a set of values, and selecting a subset of the neural signals corresponding to a neural spike, as described in further detail above with respect to operation 502 of FIG. 5. The selected subset of the neural signals can be used to perform one or more of operations 704-712, including sampling the neural signals at operation 704. Accordingly, the neural transmitter may identify a subset of the set of neural signals corresponding to a neural spike, and sample the set of samples from the identified subset of the neural signals. Spike events may be detected and selected per channel and/or based on characteristics of the spike event.

In operation 704, the neural signals are sampled to generate a set of samples. For example, spikes (detected and selected as described above) are sampled within a window of time (e.g., between 15 ms and 30 ms). The spikes may be sampled, for example, to collect a group of 8/16 samples. The neural transmitter 102, or other suitable device or subset thereof, can variously sample the neural signals. For example, the neural transmitter 102 can gather or otherwise receive 20,000 samples per second, or 500 samples in 20 milliseconds, to generate the set of samples. In other examples, the neural transmitter 102 may generate a frame or a set of samples of size 16 from the neural signals received in the operation 702. The sampling may involve the neural transmitter 102, or other suitable device or subset thereof, generating at least 10 samples, of the neural signals, at a sampling rate of from 100 to 1,000 samples per window. The window may include or otherwise be characterized by a time frame of from 10 milliseconds to 40 milliseconds. The sampling rate, the window, or a combination thereof may include or be characterized by any other suitable ranges or values (e.g., less than 100 samples per window, greater than 1,000 samples per window, less than 10 milliseconds, greater than 40 milliseconds, etc.).

In operation 706, a subset of the set of samples is identified based on a threshold value. The threshold value can be or otherwise include a value that may be close to or otherwise approximate to zero for use with sparse neural signals. In some examples, a group of 8/16 samples is collected. Each of these values is compared to the threshold value of zero. It is determined whether all of these values are zero, or if one or more of the values are nonzero.

In operation 708, a value of each sample of the subset of the set of samples is encoded using unary coding to generate an encoded value. As noted above with respect to operation 706, in some implementations, the groups of samples are sorted according to whether the samples are all zero, or if the set of samples includes on e or more nonzero values. In some examples, the neural transmitter 102 can leverage the sparse nature of the neural signals. For example, the subset of the set of samples may include mostly values that are close to or equal to zero, which may be easily encoded into the unary encoded value. In other examples, the subset of the set of samples may not include values close to or equal to zero (e.g., the neural transmitter 102 may have filtered values close to or equal to zero out of the subset), and the neural transmitter 102 can encode the subset of the set of samples into the unary encoded value. If all the values in the set of samples are zero, a 0 may be appended to a bit-stream. If one or more values in the set of samples are nonzero, a 1 may be appended to the bit-stream, and each value is encoded. In some implementations, each value is encoded using unary coding, as described above with respect to operation 510 of FIG. 5.

In operation 710, the encoded value is appended to a bit-stream for each of the identified subset. Each identified subset may correspond to sets of samples having one or more nonzero values. Accordingly, sets of samples having all zero values are refrained from being transmitted. This technique is particularly useful for neural signals due to their sparse nature, where many sets of zero signals are commonly detected. The neural transmitter 102 may encode a subset of the set of samples for each of the neural spikes included in neural signals received in the operation 702. The neural transmitter 102 can append the encoded values for each of the identified subsets to the bit-stream. For example, after appending a 1 to the bit-stream and encoding each value with unary coding, the encoded value is appended to the bit-stream. Operations 702-710 can be used to count how many spikes each channel detected over a given time window. This is advantageous for neural signals in that normally about 85% of neural signal values detected are zero. The values that are nonzero can be appended using unary coding, which is particularly useful for the neural signal application since nonzero values are skewed towards being very small for neural signals, which is a suitable use-case for unary coding. Alternatively, other encoding techniques such as rANS can be implemented, although unary coding has been found adequate for most neural signal applications. Alternatively, or additionally, dictionary-based compression techniques are used. For example, Lempel-Ziv-Welch compression can be used, as described in "Lempel-Ziv-Welch," NIST, https://xlinux.nist.gov/dads/HTML/lempelZivWelch.html. In some examples, the operations 702-710 can achieve a compression ratio of approximately 5:1.

In operation 712, the bit-stream is transmitted. The neural transmitter 102 can transmit the bit-stream for further processing. For example, the neural transmitter 102 can transmit the bit-stream to a separate computing device using a short-range communication system or network. In some examples, the separate computing device can decode the bit-stream in an equal-but-opposite process compared to the encoding (e.g., as described above with respect to operations 704-710). The separate computing device can use the decoded bit-stream (e.g., the neural signals) to perform analysis, for example, with respect to the entity 100 or to perform any other suitable operations.

Figure 8:
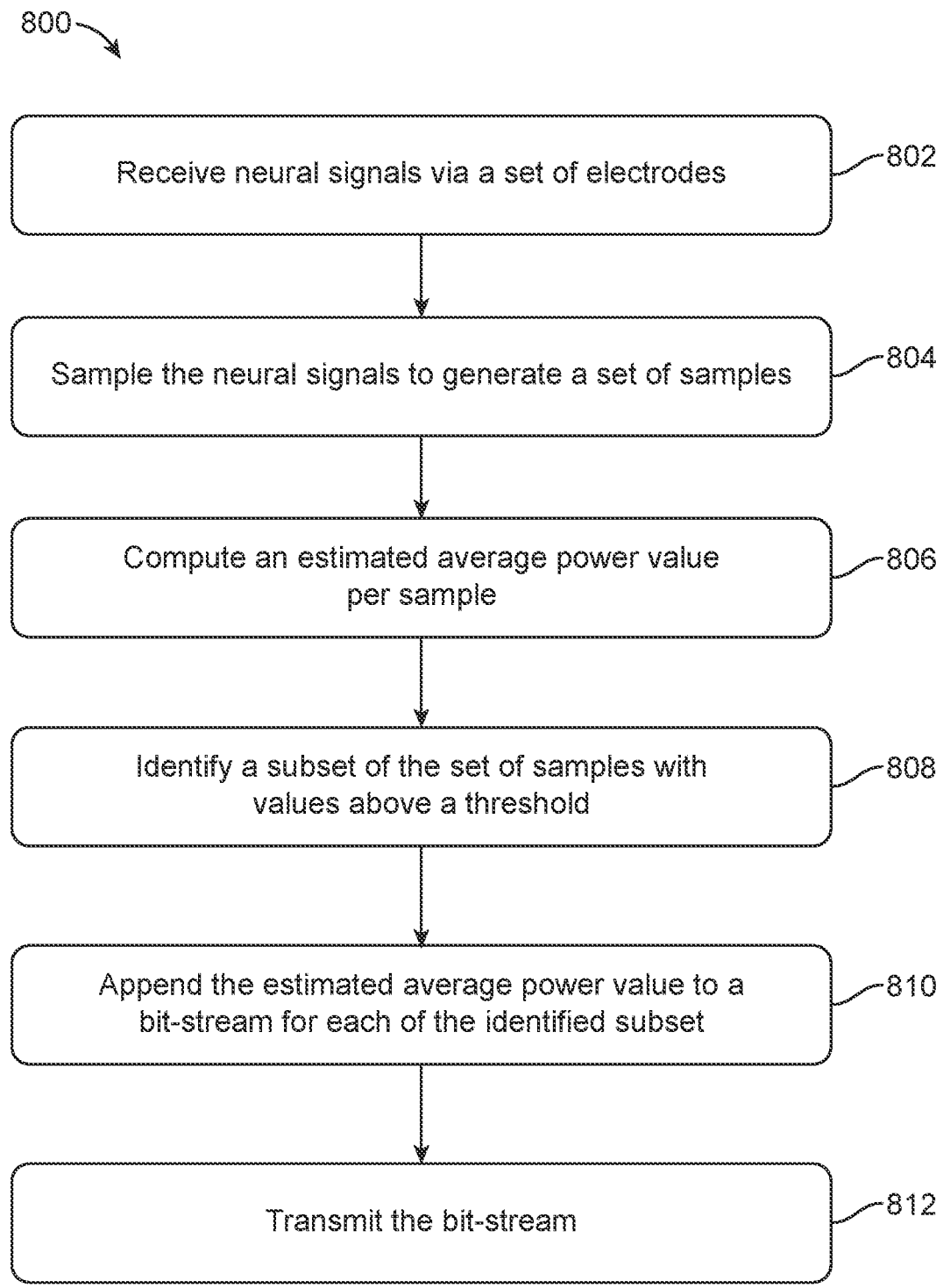
FIG. 8 is a flowchart of another example of a process to compress and transmit sparse neural signals in accordance with an embodiment.

FIG. 8 is a flowchart of another example of a process 800 to compress and transmit sparse neural signals in accordance with an embodiment. In some examples, the process 800 can be used with respect to a spike-band power operational mode of the neural transmitter 102. One or more operations of the process 800 can be performed by the neural transmitter 102, any component thereof, or any other suitable device (e.g., computing device) suitably coupled to the neural transmitter 102.

In operation 802, neural signals are received from one or more electrodes. The electrodes can be included in, or otherwise (e.g., communicatively or electrically) coupled, to the neural transmitter 102. In some examples, the electrodes can detect neural signals (e.g., spikes) from the entity 100 (or any component thereof such as a brain of the entity 100). The electrodes may detect or otherwise receive the neural signals and may transmit the neural signals to the neural transmitter 102 for processing (e.g., compressing).

In some embodiments, the neural transmitter 102 may filter the neural signals. For example, the neural transmitter 102 filters a wave form corresponding to the neural signals to identify and select portions of the wave form corresponding to neural spikes. These portions of the wave form are selected. The neural transmitter 102 may use configured neural sensors to measure neural signals by applying a filter around frequency bins corresponding to neural spikes. For example, the neural transmitter 102 can filter, remove, or otherwise ignore neural signals that are not in close proximity to, or otherwise associated with, a neural spike. The filtered neural signals can be fitted, by the neural transmitter 102, to a model to compute a set of values. For example, the neural transmitter 102 can fit the filtered neural signals to a polynomial and select a subset of the neural signals, as described above and in US Patent Publication Number US20210012909A1, supra. In some examples, the neural transmitter 102 may down sample the filtered neural signals.

In operation 804, the neural signals are sampled to generate a set of samples. Each of the values may include a measured power (e.g., an amplitude). In some implementations, each sample corresponds to a channel. The values are sampled on a per-channel basis. The neural transmitter 102 may further compute an absolute value of each sampled value.

In operation 806, an average power value per sample is determined. In some examples, each sample may represent or otherwise correspond to a value included in a neural spike. Each of the values may include a measured power (e.g., an amplitude). In some examples, the neural transmitter 102 can accumulate filtered neural signals within a time window (e.g., from 10 milliseconds to 40 milliseconds or other suitable time windows). The neural transmitter 102 can determine an estimated average power value for the accumulated, filtered neural signals within the time window. In some embodiments, the neural transmitter 102 computes an average power value per channel. The neural transmitter 102 may compute a spike band power vector by storing a vector for each of the average power values per channel. For example, the neural transmitter 102 stores a vector of size n, where n is the number of channels.

In operation 808, a subset of the set of samples is identified based on a threshold value. The threshold value can be or otherwise include a value that may be close to or otherwise approximate to zero for use with sparse neural signals. For example, the threshold value is zero. For each element in the spike-band power vector, the neural transmitter 102 determines whether the element in the spike-band power vector (e.g., an average power value as determined in operation 806) is above the threshold value, i.e., nonzero.

In operation 810, a value is appended to a bit-stream for each of the identified subset. For example, for each non-zero element identified in the spike-band power vector, the neural transmitter 102 appends the corresponding power value to the bit-stream. Alternatively, or additionally, the neural transmitter 102 appends a "1" to the bit-stream for each non-zero element in the spike-band power vector. The bit-stream may include compressed neural signals (e.g., stored as average power values). In some implementations, for each nonzero element in the spike-band power vector (e.g., corresponding to values found not to exceed the threshold at operation 806), a "0" is appended to the bit-stream. In some examples, the operations 802-710 can achieve a compression ratio of approximately 30:1 when reading data out of 150 simultaneous channels.

In operation 812, the bit-stream is transmitted. The neural transmitter 102 can transmit the bit-stream for further processing. For example, the neural transmitter 102 can transmit the bit-stream to a separate computing device using a short-range communication system or network. In some examples, the separate computing device can reverse some or all of the operations 806-810 to analyze the received data. In some implementations, the separate computing device stores a mapping of channels to bits in the bit-stream used to identify the corresponding channels. The separate computing device can use the bit-stream (e.g., the neural signals) to perform analysis, for example, with respect to the entity 100 or to perform any other suitable operations.

As noted above, one or more of the processes described with respect to FIGS. 5-8 may be applied, depending on the operational mode in use. In some examples, given a collection of compression techniques (e.g., one or more of the processes 500, 600, 700, and/or 800), all are attempted, and it is determined which compression technique is the most effective for that specific dataset. In some examples, the neural transmitter 102 appends a prefix (e.g., to a bit-stream) indicating which method was used. In some examples, the neural transmitter 102 appends the data of the selected compression method. In some examples, the compression techniques described herein (e.g., the techniques described with respect to FIGS. 5-8) may be used individually or in combination with other suitable compression techniques.

In some implementations, one or more of the methods of FIG. 5, FIG. 6, FIG. 7, or FIG. 8 are used to transmit data characterizing an intent or action of the entity. Execution of machine-learning models on the neural transmitter allows for the data characterizing the intent or action to be transmitted wirelessly. The data characterizing the intent or action data can be transmitted off of the neural transmitter while refraining from transmitting additional information, achieving additional data compression. To configure the neural transmitter for such intent determination, a high-bandwidth operating mode is selected. For example, binned-spikes (as described above with respect to FIG. 7) and spike-band power modes (as described above with respect to FIG. 8) are particularly suitable due to the high amount of channels that can be transmitted simultaneously. In an initial configuration phase, compressed data is streamed to an external device while the entity performs some mental actions by following some calibration prompts. The external device will then associate the neural activity with the mental actions and generate a model that is able to compute the likelihood of a certain action being executed by the entity. This model is uploaded to the neural transmitter (e.g., via wireless communication). The neural transmitter is then able to directly translate neural activity to user actions, which achieves an effective compression ratio on the order of 100:1.

In some implementations, signal frequency decomposition is used to provide frequency components of neural signals coming from multiple channels. In some embodiments, a Haar transform is used to extract relevant frequency information. Computing a Harr transform involves computing a wavelet function of a signal, where wavelet coefficients encode information about local aspects of the signal. (See, e.g., "Haar Transform," Wikipedia, https://en.wikipedia.org/wiki/Haar_wavelet#Haar_transform). The Harr transform has the advantage of being extremely efficient computationally speaking, thus making it suitable for on-chip calculation of these coefficients. As the values for each scale of the Haar transform are generated, they are immediately squared and summed to determine the energy contained in that frequency band. One property of the Haar transform is that it will split the frequency spectrum into powers of two (e.g., bands from 10 kHz to 20 kHz, 5 kHz to 10 kHz, 2.5 kHz to 5 kHz, and so on), allowing the system to represent the frequency information of a large amount of samples with very few values. In some embodiments, a 13-scale Haar transform is used, which is able to compress data from 8192 samples into just 13 numbers. This manipulation of data is lossy, and thus suitable for when the user is interested in looking at overall frequency characteristics rather than individual samples. Alternatively, or additionally, signal frequency decomposition can be performed using algorithms such as sliding Discrete Fourier Transform (DFT) (see, e.g., Jacobsen, Eric, "Understanding and Implementing the Sliding DFT," DSP Related, https://www.dsprelated.com/showarticle/776.php (2005)), Goertzel algorithm (see, e.g., "Goertzel Algorithm," Wikipedia, https://en.wikipedia.org/wiki/Goertzel_algorithm), or sliding Goertzel algorithm (see, e.g., Jacobsen, Eric & Lyons, Richard, "The Sliding DFT," Signal Processing Magazine, IEEE. 20. 74-80.10.1109/MSP.2003.1184347, available at https://www.researchgate.net/publication/3321463_The_sliding_DFT (2003)) algorithms. The sliding DFT, Goertzel, and Sliding Goertzel algorithms are able to extract information on certain frequency bands with different degrees of accuracy and selectivity.

It should be appreciated that a brain implant or other system and a respective control system for the brain implant can have one or more microprocessors/processing devices that can further be a component of the overall apparatuses. The control systems are generally proximate to their respective devices, in electronic communication (wired or wireless) and can also include a display interface and/or operational controls configured to be handled by a user to monitor the respective systems, to change configurations of the respective systems, and to operate, directly guide, or set programmed instructions for the respective systems, and sub-portions thereof. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C #, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

In some embodiments, the systems and methods of the present disclosure can be used in connection with neurosurgical techniques. However, one skilled in the art would recognize that neurosurgical techniques are a non-limiting application, and the systems and methods of the present disclosure can be used in connection with any biological tissue. Biological tissue can include, but is not limited to, the brain, muscle, liver, pancreas, spleen, kidney, bladder, intestine, heart, stomach, skin, colon, and the like.

The systems and methods of the present disclosure can be used on any suitable multicellular organism including, but not limited to, invertebrates, vertebrates, fish, bird, mammals, rodents (e.g., mice, rats), ungulates, cows, sheep, pigs, horses, non-human primates, and humans. Moreover, biological tissue can be ex vivo (e.g., tissue explant), or in vivo (e.g., the method is a surgical procedure performed on a patient).

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. A method for compressing neural signals, the method comprising:
    receiving neural signals via a plurality of electrodes;
    sampling the neural signals to generate a set of samples;
    computing a difference between each sample and a previous sample;
    based on the computed difference between each sample and the previous sample, selecting a subset of the samples;
    encoding each sample of the subset of the samples to generate a unary encoded value and a binary encoded value for each sample; and
    transmitting the unary encoded values and the binary encoded values for further processing.

2. The method of claim 1, wherein:
    the encoding comprises, for each sample, computing a factor that minimizes a total size of the encoded sample.

3. The method of claim 2, wherein:
    each unary encoded value is a quotient computed based on the computed factor;
    each binary encoded value is a remainder corresponding to the quotient; and
    the binary encoded value is truncated before the transmitting.

4. The method of claim 1, wherein:
    the method is executed on an integrated circuit communicatively coupled to the plurality of electrodes, the electrodes implanted in a brain.

5. The method of claim 4, wherein:
    transmitting the unary encoded values and the binary encoded values further comprises transmitting the values off of the integrated circuit via short-range wireless communication system.

6. The method of claim 1, wherein sampling the neural signals comprises:
    collecting a frame of 10 or more samples at a sampling rate of between 100 to 1,000 samples per window of 10 milliseconds to 40 milliseconds.

7. A method for compressing neural signals comprising:
    receiving neural signals via a plurality of electrodes;
    sampling the neural signals to generate a set of samples;
    computing a wavelet transform based upon the set of samples to generate a wavelet representation of each sample;
    quantizing each wavelet representation to generate a bit-stream; and
    encoding the bit-stream to generate a compressed encoded representation of the neural signals.

8. The method of claim 7, further comprising:
    filtering the neural signals;
    fitting the filtered neural signals to a model to compute a set of values;
    comparing the set of values to a respective set of threshold values; and
    based on the comparison, selecting a subset of the neural signals corresponding to a neural spike, wherein the selected subset of the neural signals is used to compute the wavelet transform.

9. The method of claim 7, wherein:
computing the wavelet transform comprises computing a discrete wavelet transform.

10. The method of claim 2, wherein:
the bit-stream is encoded using range asymmetric numeral systems (rANS).

11. The method of claim 7, wherein:
the method is executed on an integrated circuit communicatively coupled to the plurality of electrodes, the plurality of electrodes implanted in a brain; and
the method further comprises transmitting the compressed encoded representation of the neural signals off of the integrated circuit via a short-range wireless communication.

12. The method of claim 7, wherein sampling the neural signals comprises:
collecting a frame of 10 or more samples at a sampling rate of between 100 to 1,000 samples per window of 10 milliseconds to 40 milliseconds.

13. A method for compressing neural signals comprising:
receiving neural signals via a plurality of electrodes;
sampling the neural signals to generate a set of samples;
identifying a subset of the set of samples with values above a threshold;
for each of the identified subset of the set of samples, appending a value associated with the subset of the set of samples to a bit-stream; and
transmitting the bit-stream for further processing.

14. The method of claim 13, further comprising, before appending the value to the bit-stream:
encoding a value of each sample, of the identified subset of the set of samples, using unary coding to generate an encoded value, wherein the encoded value is appended to the bit-stream.

15. The method of claim 13, further comprising:
identifying a subset of the neural signals corresponding to a neural spike,
wherein the set of samples is sampled from the subset of the neural signals.

16. The method of claim 15, wherein identifying the subset of the neural signals comprises:
filtering the neural signals;
fitting the filtered neural signals to a model to compute a set of values;
comparing the set of values to a respective set of threshold values; and
based on the comparison, selecting the subset of the neural signals.

17. The method of claim 15, further comprising:
computing an estimated average power value per sample, wherein the average power value is the value appended to the bit-stream.

18. The method of claim 17, further comprising:
accumulating filtered neural signals within a time window, wherein the estimated average power value is computed for the neural signals accumulated within the time window.

19. The method of claim 18, further comprising:
downsampling the filtered neural signals before the accumulating.

20. The method of claim 13, wherein the method is executed on an integrated circuit communicatively coupled to the plurality of electrodes; and
transmitting the bit-stream for further processing comprises transmitting the bit-stream off of the integrated circuit via a short-range wireless communication.

* * * * *